(12) United States Patent
Nishitani et al.

(10) Patent No.: US 11,578,166 B2
(45) Date of Patent: Feb. 14, 2023

(54) COMPOSITION FOR CURABLE RESIN, CURED PRODUCT OF SAID COMPOSITION, PRODUCTION METHOD FOR SAID COMPOSITION AND SAID CURED PRODUCT, AND SEMICONDUCTOR DEVICE

(71) Applicant: ENEOS Corporation, Tokyo (JP)

(72) Inventors: Yoshinori Nishitani, Tokyo (JP); Masaki Minami, Tokyo (JP); Tatsuki Sato, Tokyo (JP)

(73) Assignee: ENEOS Corporation, Tokyo (JP)

( * ) Notice: Subject to any disclaimer, the term of this patent is extended or adjusted under 35 U.S.C. 154(b) by 276 days.

(21) Appl. No.: 16/759,688

(22) PCT Filed: Oct. 26, 2018

(86) PCT No.: PCT/JP2018/039819
§ 371 (c)(1),
(2) Date: Apr. 27, 2020

(87) PCT Pub. No.: WO2019/083002
PCT Pub. Date: May 2, 2019

(65) Prior Publication Data
US 2020/0325270 A1      Oct. 15, 2020

(30) Foreign Application Priority Data

Oct. 27, 2017   (JP) .............................. JP2017-208595

(51) Int. Cl.
| C08G 59/26 | (2006.01) |
| C07D 265/16 | (2006.01) |
| C08G 59/24 | (2006.01) |
| C08K 3/36 | (2006.01) |
| H01L 23/29 | (2006.01) |

(52) U.S. Cl.
CPC .......... *C08G 59/26* (2013.01); *C07D 265/16* (2013.01); *C08G 59/24* (2013.01); *C08G 59/245* (2013.01); *C08K 3/36* (2013.01); *H01L 23/293* (2013.01); *H01L 23/295* (2013.01)

(58) Field of Classification Search
None
See application file for complete search history.

(56) References Cited

U.S. PATENT DOCUMENTS

| 4,395,574 A | 7/1983 | Doorakian et al. |
| 2009/0215967 A1* | 8/2009 | Lin ................... C07F 9/657172 |
| | | 525/390 |
| 2012/0028047 A1 | 2/2012 | Imai et al. |
| 2014/0023839 A1 | 1/2014 | Wang et al. |
| 2018/0126701 A1 | 5/2018 | You et al. |
| 2018/0327558 A1 | 11/2018 | Li et al. |

FOREIGN PATENT DOCUMENTS

| CN | 102300936 A | 12/2011 |
| CN | 104371273 A | 2/2015 |
| EP | 3219757 A1 | 9/2017 |
| JP | S55-157594 A | 12/1980 |
| JP | 2012-036318 A | 2/2012 |
| JP | 2013-060407 A | 4/2013 |
| JP | 2015-535865 A | 12/2015 |
| JP | 2016-218433 A | 12/2016 |
| TW | 201508034 A | 3/2015 |
| WO | WO 2017/148127 A1 | 9/2017 |
| WO | WO 2017/188448 A1 | 11/2017 |
| WO | WO 2018/105743 A1 | 6/2018 |
| WO | WO 2018/181857 A1 | 10/2018 |
| WO | WO 2019/083003 A1 | 5/2019 |
| WO | WO 2019/083004 A1 | 5/2019 |

OTHER PUBLICATIONS

The International Bureau of WIPO, International Preliminary Report on Patentability in International Patent Application No. PCT/JP2018/039819 (dated May 7, 2020).
Japan Patent Office, International Search Report in International Patent Application No. PCT/JP2018/039819 (dated Jan. 15, 2019).
Korean Intellectual Property Office, Notification of Reasons for Refusal in Korean Patent Application No. 10-2020-7011954 (dated Dec. 21, 2021).
European Patent Office, Extended European Search Report in European Patent Application No. 18869962.3 (dated Jul. 19, 2021).
U.S. Appl. No. 16/759,677, filed Apr. 27, 2020.
U.S. Appl. No. 16/759,704, filed Apr. 27, 2020.
China National Intellectucal Property Administration, First Office Action in Chinese Patent Application No. 201880069498.3 (dated Apr. 19, 2022).
Taiwan Intellectual Property Office, Office Action in Taiwanese Patent Application No. 107137936 (dated May 6, 2022).

* cited by examiner

*Primary Examiner* — Megan McCulley
(74) *Attorney, Agent, or Firm* — Leydig, Voit & Mayer, Ltd.

(57) ABSTRACT

The invention relates to a curable resin composition containing (A) a multifunctional benzoxazine compound having two or more benzoxazine rings, (B) an epoxy compound having at least one norbornane structure and at least two epoxy groups, (C) a biphenyl type epoxy compound, and (D) a curing agent, and optionally (E) an inorganic filler and (F) a curing accelerator; a cured product thereof; methods of producing the curable resin composition and the cured product; and a semiconductor device in which a semiconductor element is disposed in a cured product obtained by curing a curable resin composition containing components (A) to (D), and optionally components (E) and (F).

20 Claims, No Drawings

COMPOSITION FOR CURABLE RESIN, CURED PRODUCT OF SAID COMPOSITION, PRODUCTION METHOD FOR SAID COMPOSITION AND SAID CURED PRODUCT, AND SEMICONDUCTOR DEVICE

CROSS-REFERENCE TO RELATED APPLICATIONS

This patent application is the U.S. national phase of International Patent Application No. PCT/JP2018/039819, filed Oct. 26, 2018, which claims the benefit of Japanese Patent Application No. 2017-208595, filed Oct. 27, 2017, both of which are hereby incorporated by reference in their entireties.

TECHNICAL FIELD

The present invention relates to a curable resin composition for obtaining a cured product high in heat resistance, a cured product thereof, and methods of producing the curable resin composition and the cured product. Furthermore, the present invention relates to a semiconductor device using the cured product as a sealant.

BACKGROUND ART

Curable resins are used in various applications of semiconductor sealants, fiber reinforced plastics, and the like, and benzoxazine compounds are used for one of raw materials of such resins.

Benzoxazine compounds refer to compounds each including a benzoxazine ring having a benzene backbone and an oxazine backbone, and benzoxazine resins as cured products (polymerized products) thereof are excellent in physical properties such as heat resistance and mechanical strength, and are used as high-performance materials in various applications.

Patent Literature 1 discloses a novel benzoxazine compound having a specified structure, and a production method thereof, and describes the benzoxazine compound which has a high thermal conductivity and which enables a benzoxazine resin cured product having a high thermal conductivity to be produced.

Patent Literature 2 discloses a thermosetting resin where a reactive end of a polybenzoxazine resin having a specified benzoxazine ring structure in a main chain is partially or fully closed, and describes the thermosetting resin which is excellent in storage stability in the case of being dissolved in a solvent.

RELATED ART DOCUMENTS

Patent Literature

[Patent Literature 1] JP 2013-60407 A
[Patent Literature 2] JP 2012-36318 A

SUMMARY OF THE INVENTION

Problems to be Solved by the Invention

There is still a need for a resin cured product that is higher in heat resistance and higher in mechanical strength so as to be adapted for more stringent usage conditions, in applications of, for example, matrix resins for adhesives, sealants, paints, and composites. There is a need for a curable resin composition for obtaining a cured product that is high in physical strength, particularly in applications of a semiconductor device and the like where much higher reliability is demanded.

However, there has not been obtained any curable resin composition for obtaining a cured product that can satisfy both excellent cured product performance and high mechanical strength.

Accordingly, an object of the present invention is to provide a curable resin composition for obtaining a cured product that can satisfy both high heat resistance and high mechanical strength. Another object of the present invention is to provide a cured product obtained by curing the curable resin composition, and methods of producing the curable resin composition and the cured product. Another object of the present invention is to provide a semiconductor device using the cured product as a sealant.

Means for Solving the Problems

The present inventors have made intensive studies in order to achieve the above objects, and as a result, have developed a curable resin composition containing a multifunctional benzoxazine compound and specific two kinds of epoxy compounds, and have found that a cured product of the curable resin composition is excellent in heat resistance and mechanical strength, thereby leading to completion of the present invention.

That is, the present invention is as follows.

[1] A curable resin composition containing:
(A) a multifunctional benzoxazine compound having at least two benzoxazine rings, the compound being at least one multifunctional benzoxazine compound selected from a multifunctional benzoxazine compound having a structural unit of formula (1) and a multifunctional benzoxazine compound represented by a structure of formula (2),
(B) an epoxy compound having at least one norbornane structure and at least two epoxy groups,
(C) a biphenyl type epoxy compound, and
(D) a curing agent;

[Chem 1]

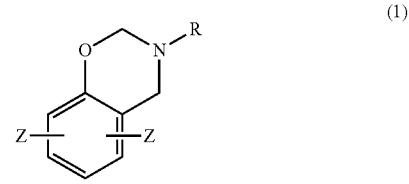

(1)

wherein in the formula (1), R represents a linear alkyl group having 1 to 12 carbon atoms, a cyclic alkyl group having 3 to 8 carbon atoms, or an aryl group having 6 to 14 carbon atoms, where the aryl group optionally has halogen or a linear alkyl group having 1 to 12 carbon atoms, as a substituent; and each Z represents hydrogen, a hydrocarbon group having 1 to 8 carbon atoms and/or a linking group and is optionally the same or different, at least one Z represents a linking group, and benzoxazine rings are linked by the linking group;

[Chem 2]

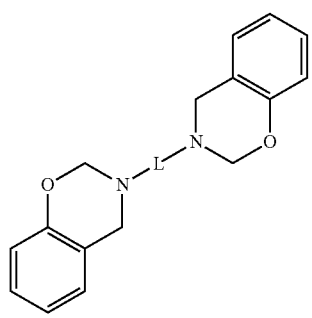
(2)

wherein in the formula (2), L represents a divalent organic group having 1 to 5 aromatic rings or an alkylene group having 2 to 10 carbon atoms, and the organic group and the alkylene group optionally comprise oxygen and/or sulfur.

[2] The curable resin composition according to [1], wherein (C) the biphenyl type epoxy compound is an epoxy compound represented by a structure of formula (3-1) or (3-2):

[Chem 3]

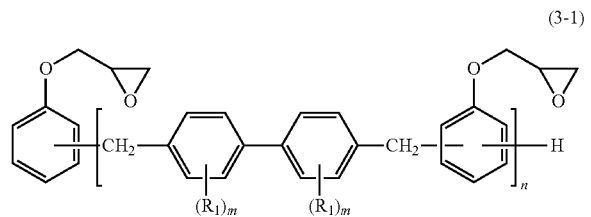
(3-1)

wherein in the formula (3-1), each substituent represents an alkyl group having 1 to 4 carbon atoms, optionally being the same or different; m represents the number of the substituent(s) $R_1$ and is an integer of 0 to 4; and n represents an average value and is 1 to 10;

[Chem 4]

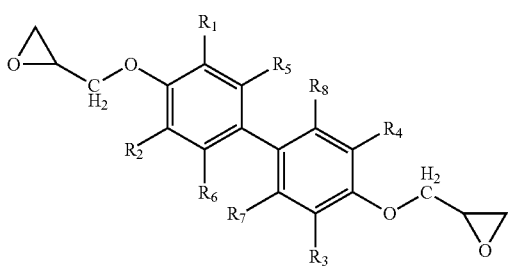
(3-2)

wherein in the formula (3-2), $R_1$ to $R_8$ represent a hydrogen atom, a halogen atom, or an alkyl group having 1 to 4 carbon atoms, and are each optionally the same or different.

[3] The curable resin composition according to [1] or [2], further containing (E) an inorganic filler.

[4] The curable resin composition according to any of [1] to [3], further containing (F) a curing accelerator,

[5] A cured product obtained by curing the curable resin composition according to any of [1] to [4].

[6] A semiconductor device, wherein a semiconductor element is disposed in a cured product obtained by curing the curable resin composition according to any of [1] to [4].

[7] A method of producing a curable resin composition, the method comprising the steps of: mixing (A) a multifunctional benzoxazine compound having at least two benzoxazine rings, the compound being at least one multifunctional benzoxazine compound selected from a multifunctional benzoxazine compound having a structural unit of formula (1) and a multifunctional benzoxazine compound represented by a structure of formula (2), (B) an epoxy compound having at least one norbornane structure and at least two epoxy groups, (C) a biphenyl type epoxy compound, and (D) a curing agent, to obtain a mixture; and processing the mixture into a powdery, pelletized, or granular curable resin composition;

[Chem 5]

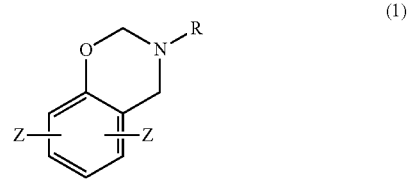
(1)

wherein in the formula (1), R represents a linear alkyl group having 1 to 12 carbon atoms, a cyclic alkyl group having 3 to 8 carbon atoms, or an aryl group having 6 to 14 carbon atoms, where the aryl group optionally has halogen or a linear alkyl group having 1 to 12 carbon atoms, as a substituent; and each Z represents hydrogen, a hydrocarbon group having 1 to 8 carbon atoms and/or a linking group and is optionally the same or different, at least one Z represents a linking group, and benzoxazine rings are linked by the linking group;

[Chem 6]

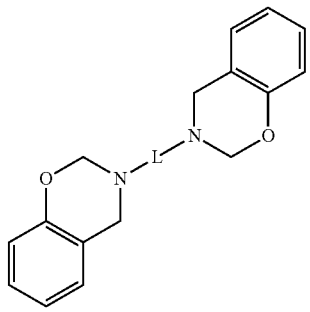
(2)

wherein in the formula (2), L represents a divalent organic group having 1 to 5 aromatic rings or an alkylene group having 2 to 10 carbon atoms, and the organic group and the alkylene group optionally comprise oxygen and/or sulfur.

[8] The production method according to [7], wherein (C) the biphenyl type epoxy compound is an epoxy compound represented by a structure of formula (3-4) or (3-2):

[Chem 7]

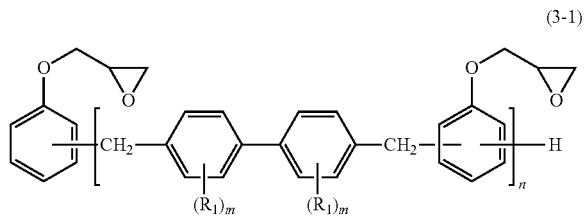

(3-1)

wherein in the formula (3-1), each substituent $R_1$ represents an alkyl group having 1 to 4 carbon atoms, optionally being the same or different; m represents the number of the substituent(s) $R_1$ and is an integer of 0 to 4; and n represents an average value and is 1 to 10;

[Chem 8]

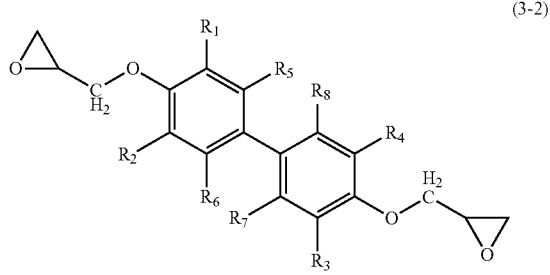

(3-2)

wherein in the formula (3-2), $R_1$ to $R_8$ represent a hydrogen atom, a halogen atom, or an alkyl group having 1 to 4 carbon atoms, and are each optionally the same or different.

[9] The production method according to [7] or [8], wherein the step of obtaining a mixture includes further mixing (E) an inorganic filler and/or (F) a curing accelerator to obtain a mixture, [10] A method of producing a cured product, the method comprising a step of heating the curable resin composition produced by the method according to any of [7] to [9], at 150 to 300° C. for 20 seconds to 1 hour for curing.

Effects of the Invention

The curable resin composition of the present invention is a novel curable resin composition containing components (A) to (D), and further, if desired, components (E) and (F), and a cured product of the composition is characterized by being excellent in heat resistance and mechanical strength. Accordingly, the curable resin composition of the present invention can be used in an application where high heat resistance and high mechanical strength are required, for example, applications of matrix resins for adhesives, sealants, paints, and composites. In particular, the curable resin composition not only can allow a semiconductor element sealant to exert excellent sealing performance, but also can contribute to high reliability of a semiconductor device.

MODE FOR CARRYING OUT THE INVENTION

[Curable Resin Composition]

Hereinafter, the present invention will be described in detail. It is noted that each "compound" in components (A) to (C) in the present invention encompasses not only a monomer represented in each formula, but also an oligomer obtained by polymerization of a small amount of the monomer, namely, a prepolymer before formation of a curable resin.

(Component A)

The component (A) that constitutes the curable resin composition is at least one multifunctional benzoxazine compound having at least two benzoxazine rings, selected from a multifunctional benzoxazine compound having a structural unit of formula (1) and a multifunctional benzoxazine compound represented by a structure of formula (2). Herein, each Z in the formula (1) represents hydrogen, a substituent and/or a linking group (spacer), and is optionally the same or different, at least one Z represents a linking group, and benzoxazine rings are linked by the linking group. The linking group here encompasses two benzoxazine rings directly bound via no other group. Examples of the substituent include a hydrocarbon group having 1 to 8 carbon atoms.

Accordingly, the formula (1) represents the structural unit of any compound where two or more benzoxazine rings are linked at a benzene ring moiety, among options of the component (A).

The multifunctional benzoxazine compound of formula (1) can be more specifically represented as having a structure represented by formula (1a):

[Chem 9]

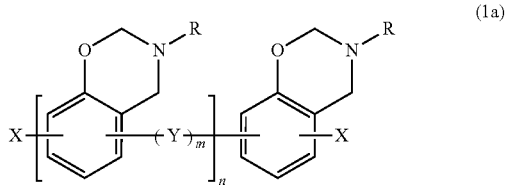

(1a)

wherein in the formula (1a), R represents a linear alkyl group having 1 to 12 carbon atoms, a cyclic alkyl group having 3 to 8 carbon atoms, or an aryl group having 6 to 14 carbon atoms, where the aryl group optionally has halogen or a linear alkyl group having 1 to 12 carbon atoms, as a substituent; each R is optionally the same or difficult; each X represents hydrogen or a hydrocarbon group having 1 to 8 carbon atoms, and is optionally the same or difficult; Y represents an alkylene group having 1 to 6 carbon atoms, oxygen, sulfur, a $SO_2$ group, or a carbonyl group; m is 0 or 1; and n is an integer of 1 to 10.

Specific examples of R in formulae (1) and (1a) can include the following groups.

Examples of the linear alkyl group having 1 to 12 carbon atoms include a methyl group, an ethyl group, a propyl group, an isopropyl group, an n-butyl group, an isobutyl group, and a t-butyl group.

Examples of the cyclic alkyl group having 3 to 8 carbon atoms include a cyclopentyl group and a cyclohexyl group.

Examples of the aryl group having 6 to 14 carbon atoms include a phenyl group, a 1-naphthyl group, a 2-naphthyl group, a phenanthryl group, and a biphenyl group.

The aryl group having 6 to 14 carbon atoms is optionally substituted, and examples of the substituent include a linear alkyl group having 1 to 12 carbon atoms, or halogen. Examples of the aryl group having 6 to 14 carbon atoms, substituted with a linear alkyl group having 1 to 12 carbon atoms, or halogen include an o-tolyl group, a m-tolyl group, a p-tolyl group, a xylyl group, an o-ethylphenyl group, a m-ethylphenyl group, a p-ethylphenyl group, an o-t-butylphenyl group, a m-t-butylphenyl group, a p-t-butylphenyl group, an o-chlorophenyl group, and an o-bromophenyl group.

R is preferably selected from a methyl group, an ethyl group, a propyl group, a phenyl group, and a p-tolyl group from the viewpoint of favorable handleability.

The component (A) may also be a mixture of a plurality of kinds of compounds represented in formula (1) or (1a), which are different in R from each other.

Examples of the hydrocarbon group having 1 to 8 carbon atoms as X in formulae (1) and (1a) include an alkyl group, an aryl group, and an aralkyl group, and an aryl group is preferable.

Examples of the multifunctional benzoxazine compound represented by formula (1) or (1a) can include a compound represented by the following formula (1X) and an oligomer obtained by polymerization of a small amount of the compound.

[Chem 10]

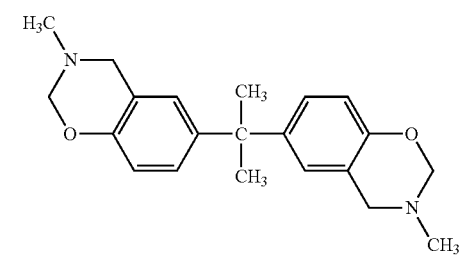
(1X)

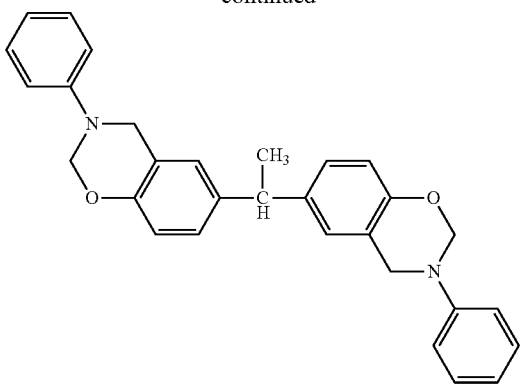

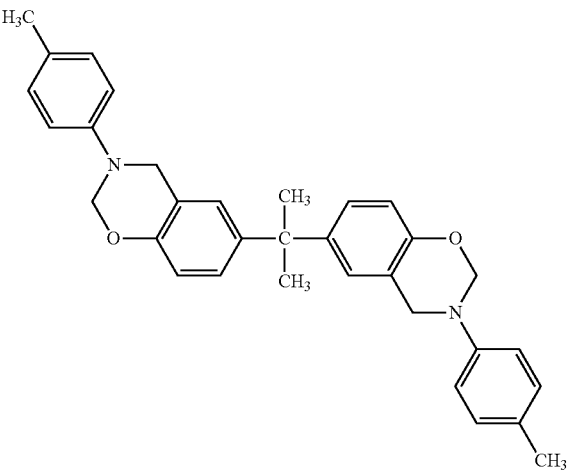

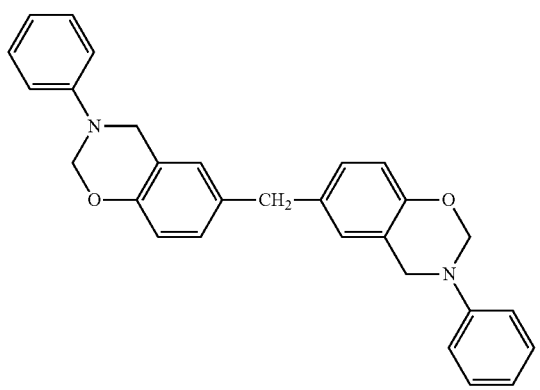

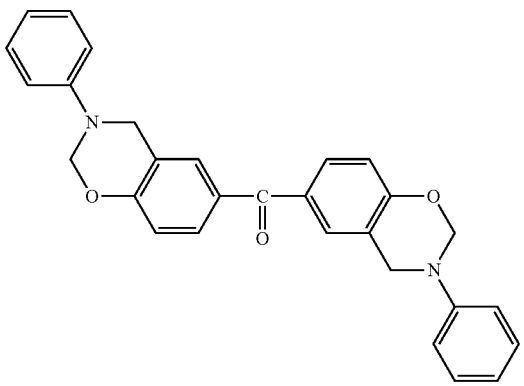

-continued

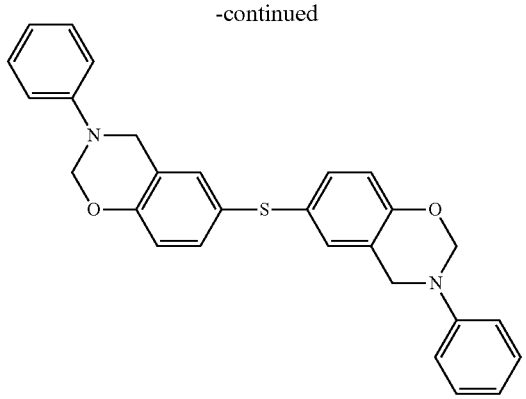

The multifunctional benzoxazine compound of formula (2), as other option of the component (A), is a compound where respective nitrogen atoms (N atoms) in two benzoxazine rings are bound via a linking group L,

[Chem 11]

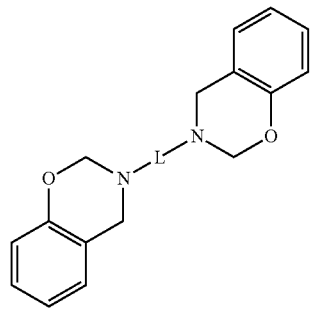

(2)

wherein in the formula (2), L represents a divalent organic group having 1 to 5 aromatic rings or an alkylene group having 2 to 10 carbon atoms, and the organic group and the alkylene group optionally comprise oxygen and/or sulfur.

The composition of the present invention may contain a plurality of kinds of multifunctional benzoxazine compounds represented by formula (2), which are different in L, in the component (A).

In the case where L in formula (2) represents an aromatic ring-containing group, the group contains 1 to 5 aromatic rings, and examples thereof include a monocyclic compound, a multicyclic compound, and a fused ring compound, L may also comprise at least one selected from the group consisting of oxygen and sulfur.

Specific examples can include a group represented by the following formula (2a).

[Chem 12]

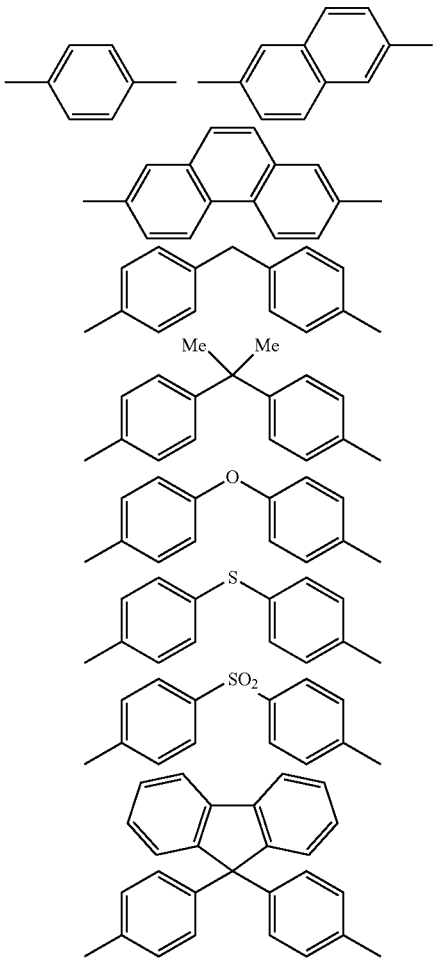

(2a)

In the case where L in formula (2) represents an alkylene group, the alkylene group has, for example, 1 to 10 carbon atoms, preferably 1 to 6 carbon atoms. Specific examples of the alkylene group include a methylene group, an ethylene group, and an isopropylidene group, and preferably include a methylene group.

Examples of the multifunctional benzoxazine compound of formula (2) can include a compound represented by the following formula (2X), and an oligomer obtained by polymerization of the compound, for example, an oligomer obtained by polymerization of a small amount of the compound.

[Chem 13]

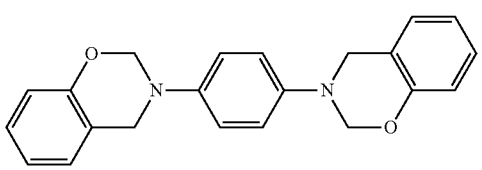

(2X)

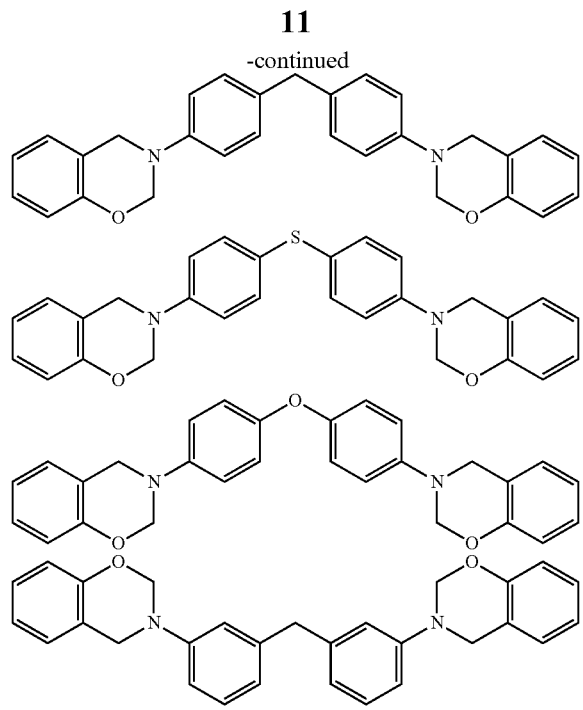

Any commercially available product can also be used as the multifunctional benzoxazine compound in the component (A).

Examples of such any commercially available product can include bisphenol F-aniline (F-a)-type benzoxazine and phenol-diaminodiphenylmethane (P-d)-type benzoxazine (both are manufactured by SHIKOKU CHEMICALS CORPORATION).

(Component B)

The component (B) that constitutes the curable resin composition is an epoxy compound having at least one norbornane structure and at least two epoxy groups (hereinafter, also simply referred to as "multifunctional epoxy compound"). The composition of the present invention may contain a plurality of kinds of the multifunctional epoxy compounds in the component (B). The epoxy compound is preferably an alicyclic epoxy compound, more preferably has an epoxy structure represented by the following formula (4), bound to a 5-membered ring, a 6-membered ring or a norbornane ring,

[Chem 14]

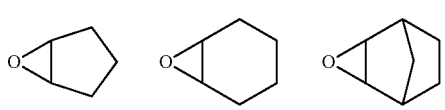

(4)

Specific examples of the alicyclic epoxy compound can include a compound represented by the following formula (5),

[Chem 15]

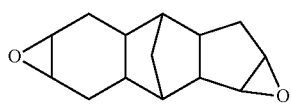

(5)

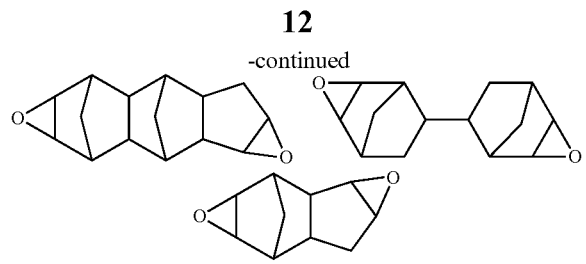

A production example of the multifunctional epoxy compound in the component (B) is described.

A compound of the following formula (5-4) can be produced by, for example, synthesizing a compound (a) having the following norbornane structure, by a Diels-Alder reaction of butadiene and dicyclopentadiene, and then reacting the compound (a) and meta-chloroperbenzoic add, as represented in the following formula (6).

[Chem 16]

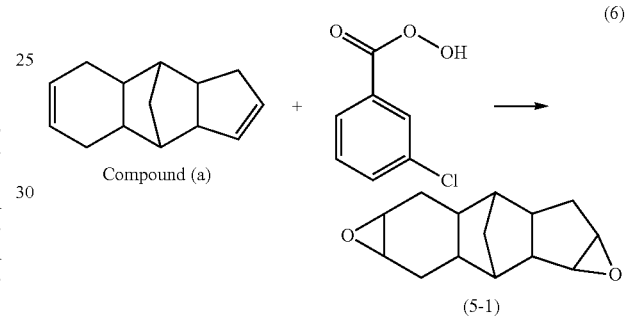

(6)

A compound of the following formula (5-2) can be produced by, for example, synthesizing a compound (b) (tricyclopentadiene) having the following norbornane structure, by a Diels-Alder reaction of cyclopentadiene and dicyclopentadiene, and then reacting the compound (b) and meta-chloroperbenzoic add, as represented in the following formula (7).

[Chem 17]

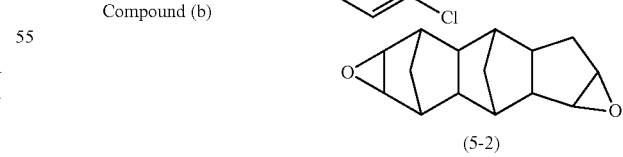

(7)

A compound of the following formula (5-3) can be produced by, for example, synthesizing a compound (c) having the following norbornane structure, by a Diels Alder reaction of butadiene and cyclopentadiene, and then reacting the compound (c) and meta-chloroperbenzoic add, as represented in the following formula (8).

[Chem 18]

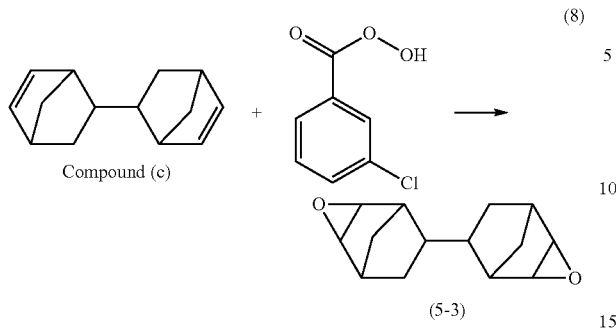

(8)

A compound of the following formula (5-4) can be produced by, for example, reacting dicyclopentadiene and potassium peroxymonosulfate (ozone). The compound of formula (5-4), dicyclopentadiene diepoxide, may also be any commercially available product, and examples of such any commercially available product can include dicyclopentadiene diepoxide manufactured by SHANDONG QIHUAN BIOCHEMICAL CO., LTD.

[Chem 19]

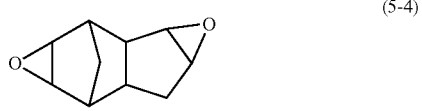

(5-4)

(Component C)

The component (C) that constitutes the curable resin composition is a biphenyl type epoxy compound. The biphenyl type epoxy compound is preferably an epoxy compound represented by a structure of the following formula (3-1) or (3-2): As of the component (C), any one of an epoxy compound represented by a structure of the following formula (3-1) and an epoxy compound represented by a structure of the following formula (3-2) may be used singly, or the two kinds of compounds may be used in mixture. The biphenyl type epoxy compound is more preferably an epoxy compound represented by a structure of the following formula (3-1):

[Chem 20]

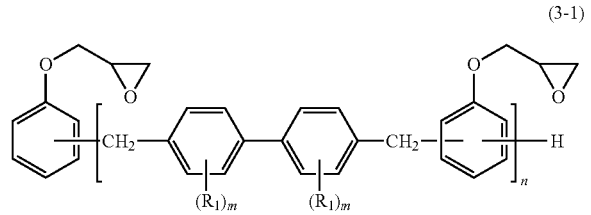

(3-1)

wherein in the formula (3-1), each $R_1$ is substituent, being an alkyl group having 1 to 4 carbon atoms, optionally being the same or different; m represents the number of the substituent(s) $R_1$ and is an integer of 0 to 4; and n represents an average value and is 1 to 10;

[Chem 21]

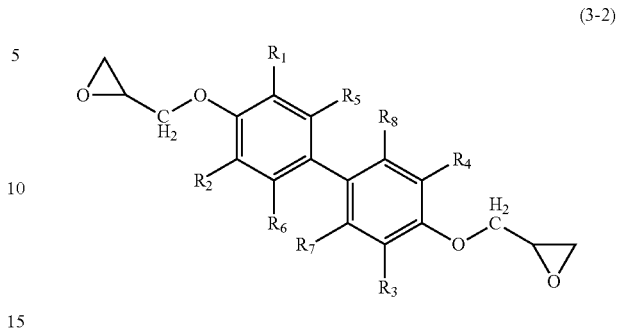

(3-2)

wherein in the formula (3-2), $R_1$ to $R_8$ represent a hydrogen atom, a halogen atom, or an alkyl group having 1 to 4 carbon atoms, and are each optionally the same or different.

In formula (3-1), m is preferably 0 to 2, more preferably 0. In formula (3-1), n is preferably 1 to 5, more preferably 2 to 4. Examples of the alkyl group having 1 to 4 carbon atoms as the substituent $R_1$ in formula (3-1) include a methyl group, an ethyl group, a propyl group, a butyl group, and the like. The substituent $R_1$ is preferably a methyl group or an ethyl group. The component (C) may also be a mixture of compounds represented by formula (3-1), wherein the compounds are different from each other in $R_1$, m, and n in the formula.

Examples of the alkyl group having 1 to 4 carbon atoms as $R_1$ to $R_8$ in formula (3-2) include a methyl group, an ethyl group, a propyl group, a butyl group, and the like, $R_1$, $R_2$, $R_3$, $R_4$, $R_5$, $R_6$, $R_7$, and $R_8$ are each preferably a hydrogen atom or a methyl group. The component (C) may also be a mixture of compounds represented by formula (3-2), wherein the compounds are different from each other in $R_1$ to $R_8$ in the formula.

In another preferred embodiment of the present invention, a biphenyl type epoxy compound used in the present invention is represented by formula (3-2) wherein $R_1$, $R_2$, $R_3$, and $R_4$ are each an alkyl group having 1 to 4 carbon atoms, and $R_5$, $R_6$, $R_7$, and $R_8$ are each a hydrogen atom. In yet another preferred embodiment of the present invention, a biphenyl type epoxy compound used in the present invention is represented by formula (3-2) wherein $R_1$, $R_2$, $R_3$, and $R_4$ are each a methyl group, and $R_5$, $R_6$, $R_7$, and $R_8$ are each a hydrogen atom.

Any commercially available product can also be used as the biphenyl type epoxy compound in the component (C). Examples of commercially available products of epoxy compounds represented by a structure of formula (3-1) include NC3000 (a tradename; from NIPPON KAGAKUYAKUHIN CO., LTD; having an epoxy equivalent of 265 to 285 g/eq), NC3000-L (a tradename; from NIPPON KAGAKUYAKUHIN CO., LTD; having an epoxy equivalent of 261 to 282 g/eq), NC3000-H (a tradename; from NIPPON KAGAKUYAKUHIN CO., LTD; having an epoxy equivalent of 280 to 300 g/eq), NC3000-FH-75M (a tradename; from NIPPON KAGAKUYAKUHIN CO., LTD; having an epoxy equivalent of 310 to 340 g/eq), NC3100 (a tradename; from NIPPON KAGAKUYAKUHIN CO., LTD.; having an epoxy equivalent of 245 to 270 g/eq), and the like. Examples of commercially available products of epoxy compounds represented by a structure of formula (3-2) include YX4000 (a tradename; from MITSUBISHI CHEMICAL CORPORATION; having an epoxy equivalent of 180 to 192 g/eq), YX4000H (a tradename; from MIT- SUBISHI CHEMICAL CORPORATION; having an epoxy equivalent of 187 to 197 g/eq), YL6121H (a tradename; from MITSUBISHI CHEMICAL CORPORATION; having an epoxy equivalent of 170 to 180 g/eq), and the like. These may be used singly or in combination of two or more kinds thereof.

The compounding ratio between the multifunctional benzoxazine compound in the component (A) and the total of the multifunctional epoxy compound in the component (B) and the biphenyl type epoxy compound in the component (C) is preferably 5 parts by mass or more and 150 parts by mass or less, more preferably 30 parts by mass or more and 130 parts by mass or less, in terms of the compounding ratio of the total of the components (B) and (C) based on 100 parts by mass of the component (A).

The compounding ratio between the component (A) and the total of the components (B) and (C) can be in the above range, thereby affording a cured product more excellent in heat resistance and mechanical strength.

In the case where the composition of the present invention contains a plurality of kinds of the multifunctional benzoxazine compounds in the component (A), the total of such compounds is assumed to be 100 parts by mass. In the case where the composition of the present invention contains a plurality of kinds of the multifunctional epoxy compounds in the component (B), the "compounding ratio of the component (B)" means the total ratio of such a plurality of compounds. Further in the case where the composition of the present invention contains a plurality of kinds of the biphenyl type epoxy compounds in the component (C), the "compounding ratio of the component (C)" means the total ratio of such a plurality of compounds.

The compounding ratio (mass ratio) of the multifunctional epoxy compound in the component (B) to the biphenyl type epoxy compound in the component (C) (the epoxy compound in the component (B): the biphenyl type epoxy compound in the component (C)) is preferably 95:5 to 5:95, more preferably 90:10 to 10:90, still more preferably 90:10 to 60:40 or 90:10 to 55:45, yet more preferably 80:20 to 60:40 or 80:20 to 55:45. The compounding ratio between the component (B) and the component (C) can be in the above range, thereby affording a cured product more excellent in heat resistance and mechanical strength.

In the case where the composition of the present invention contains a plurality of kinds of the multifunctional epoxy compounds in the component (B), the compounding amount of the component (B) means the total compounding amount of such a plurality of compounds. Further in the case where the composition of the present invention contains a plurality of kinds of the biphenyl type epoxy compounds in the component (C), the compounding amount of the component (C) means the total compounding amount of such a plurality of compounds.

(Component D)

The component (D) that constitutes the curable resin composition is a curing agent.

Specific examples of the component (D) include aromatic amines (for example, diethyltoluenediamine, metaphenylenediamine, diaminodiphenylmethane, diaminodiphenylsulfone, metaxylenediamine, and derivatives thereof), aliphatic amines (for example, triethylenetetramine and isophoronediamine), imidazoles (for example, imidazole and imidazole derivatives), dicyandiamide, tetramethylguanidine, carboxylic anhydrides (for example, methylhexahydrophthalic anhydride), carboxylic acid hydrazides (for example, adipic acid hydrazide), carboxylic acid amides, monofunctional phenols, multifunctional phenol compounds (for example, bisphenol A, bisphenol F, dihydroxynaphthalene, bisphenol sulfides (for example, bis(4-hydroxyphenyl) sulfide), and a polyphenol compound (for example, pyrogallol)), polymercaptans, carboxylates, and Lewis acid complexes (for example, boron trifluoride ethylamine complex). The component (D) is preferably at least one selected from imidazoles, aromatic amines, and multifunctional phenol compounds. These may be used singly or as a mixture of two or more kinds thereof.

The compounding ratio of the component (D) is preferably in a range of 1 part by mass or more and 30 parts by mass or less, more preferably in a range of 5 parts by mass or more and 25 parts by mass or less, in terms the compounding ratio of the component (D) based on 100 parts by mass in total of the components (A), (B), and (C). The component (D) can be contained in such a range, thereby allowing for more efficient progression of a curing reaction, and obtaining a cured product more excellent in heat resistance.

In the present invention, an "epoxy equivalent ratio" in the curable resin composition refers to [the total number of epoxy groups in the components (B) and (C)]/[the number of cyanato groups in the component (A)+the number of hydroxyl groups in the component (D)].

The epoxy equivalent ratio in the curable resin composition is preferably 0.5 or more and 1.5 or less, more preferably 0.7 or more and 1 or less. The epoxy equivalent ratio can be in the above range, thereby affording a cured product more excellent in heat resistance and mechanical strength.

(Component E)

The curable resin composition of the present invention may further contain, if desired, (E) an inorganic filler.

For example, in the case of use of the curable resin composition of the present invention in a sealant application of a semiconductor element or the like, the component (E) is preferably contained. The inorganic filler for use in the present invention is not particularly limited, and can be selected in consideration of an application of the curable resin composition or a cured product thereof, or characteristics to be provided. Hereinafter, the inorganic filler is referred to as "component (E)".

Examples of the component (E) include oxides such as silica, alumina, titanium oxide, zirconium oxide, magnesium oxide, cerium oxide, yttrium oxide, calcium oxide, antimony trioxide, zinc oxide and iron oxide; carbonates such as calcium carbonate, magnesium carbonate, barium carbonate and strontium carbonate; sulfates such as barium sulfate, aluminum sulfate and calcium sulfate; nitrides such as aluminum nitride, silicon nitride, titanium nitride, boron nitride and manganese nitride; silicon compounds such as calcium silicate, magnesium silicate and aluminum silicate; boron compounds such as aluminum borate; zirconium compounds such as barium zirconate and calcium zirconate; phosphorus compounds such as zirconium phosphate and magnesium phosphate; titanium compounds such as strontium titanate, calcium titanate, magnesium titanate, bismuth titanate, barium titanate and potassium titanate; minerals such as mica, talc, kaolin, kaolin day, kaolinite, halloysite, cordierite, pyrophyllite, montmorillonite, sericite, arnesite, bentonite, asbestos, wollastonite, sepiolite, xonotlite, zeolite, hydrotalcite, hydrated gypsum, alum, diatomaceous earth and boehmite; fly ash, dewatered sludge, glass beads, glass fibers, silica sand, magnesium oxysulfate, silicon oxide, and silicon carbide; metals such as copper, iron, cobalt and nickel, or alloys including any of such metals; magnetic materials such as sendust, alnico magnet and ferrite; and graphite and coke. The component (E) is preferably silica or alumina. Examples of the silica include molten silica, spherical silica, crystalline silica, amorphous silica, synthetic silica and hollow silica, and spherical silica and crystalline silica are preferable. The component (E) may be used singly or in combination of two or more kinds thereof.

The component (E) may be particulate, and in such a case, the average particle size is not particularly limited, and may be, for example, 0.01 µm or more and 150 µm or less, preferably 0.1 µm or more and 120 µm or less, more preferably 0.5 µm or more and 75 µm or less. Such a range leads to an improvement in packing ability into a mold cavity in use of the composition of the present invention in, for example, a sealant application of a semiconductor element. The average particle size of the component (E) can be measured by a laser diffraction/scattering method. Specifically, the average particle size can be determined by creating the particle size distribution of the inorganic filler on a volume basis, with a laser diffraction-type particle size distribution measuring apparatus, and defining the median size as the average particle size. A measurement sample that can be here used is preferably obtained by ultrasonically dispersing the inorganic filler in water. The laser diffraction-type particle size distribution measuring apparatus that can be here used is, for example, "LA-500", "LA-750", "LA-950" or "LA-960" manufactured by HORIBA LTD.

The compounding ratio of the component (E) is not particularly limited and can be appropriately selected depending on its application as long as a cured product of the curable resin composition, high in heat resistance, is obtained. For example, in the case of use of the composition in a semiconductor-sealing application, the following compounding ratio is preferable.

The lower limit value of the compounding ratio of the component (E) is, for example, 150 parts by mass or more, preferably 400 parts by mass or more, more preferably 500 parts by mass or more, based on 100 parts by mass in total of the components (A), (B), (C) and (D). The upper limit value of the compounding ratio of the component (E) is, for example, 1300 parts by mass or less, preferably 1150 parts by mass or less, more preferably 950 parts by mass or less. The lower limit value of the compounding ratio of the component (E) is 400 parts by mass or more, thereby enabling an increase in amount of moisture absorption and a reduction in strength according to curing of the curable resin composition to be more suppressed, and thus enabling a cured product having more favorable solder cracking resistance to be obtained. The upper limit value of the compounding ratio of the component (E) is 1300 parts by mass or less, thereby allowing the curable resin composition to have better fluidity and thus be easily packed into a mold, resulting in exertion of favorable sealing performance of a cured product.

(Component F)

The curable resin composition of the present invention may further contain, if desired, (F) a curing accelerator.

A known curing accelerator can be used as the curing accelerator, and examples include amine-based compounds such as tributylamine and 1,8-diazabicyclo(5,4,0)undecene-7, imidazole-based compounds such as 2-methylimidazole, 2-ethylimidazole and 1,2-dimethylimidazole, and phosphororganic compounds including phosphororganic compounds with phosphorus bound by only a covalent bond, such as triphenylphosphine, and salt-type phosphororganic compounds with phosphorus bound by a covalent bond and an ionic bond, such as tetraphenylphosphonium tetraphenylborate, but are not limited thereto. The above curing accelerators may be used singly or in combination of two or more kinds thereof. In particular, phosphororganic compounds such as triphenylphosphine and tetraphenylphosphonium tetraphenylborate exert a high effect of enhancing the speed of curing and thus are preferable.

Such a phosphororganic compound described above exerts a function of promoting a crosslinking reaction of an epoxy group and a phenolic hydroxyl group, as described in JP-S 55-157594 A. Furthermore, such a phosphororganic compound described above also exerts a function of promoting a reaction of a hydroxyl group and an epoxy group generated in a cleavage reaction of (A) the multifunctional benzoxazine compound at high temperatures. The phosphororganic compound in the present invention is not particularly limited as long as it has the above functions.

The compounding ratio of the component (F) is preferably in a range of 0.01 part by mass or more and 10 parts by mass or less, more preferably in a range of 0.1 parts by mass or more and 7 parts by mass or less, in terms the compounding ratio of the component (F) based on 100 parts by mass in total of the components (A), (B), and (C). The component (F) can be contained in such a range, thereby providing a curable resin composition having more favorable fast curability.

(Other Component(s))

The composition of the present invention may contain a benzoxazine compound other than the component (A) as long as the effects of the present invention are not impaired. For example, in the case where the composition is demanded to be reduced in viscosity, a monofunctional benzoxazine compound having one benzoxazine ring may be added to the composition.

For example, nano-carbon, a flame retardant, a release agent, a colorant, a low-stress additive, a metal hydroxide, and/or the like can be compounded into the curable resin composition of the present invention as long as performances of the curable resin composition are not impaired.

Examples of the nano-carbon include carbon nanotube, fullerene or respective derivatives.

Examples of the flame retardant include red phosphorus, phosphates such as triphenyl phosphate, tricresyl phosphate, trixylenyl phosphate, cresyl diphenyl phosphate, xylenyl diphenyl phosphate, resorcinol bis-phenyl phosphate, bisphenol A bis-diphenyl phosphate, borates, and phosphazene.

Examples of release agents include: stearates; natural waxes such as carnauba wax; synthetic waxes such as oxidized polyethylene wax; higher fatty adds such as stearic acid or esters of the higher fatty adds; metal salts such as zinc stearate; paraffin; and silicone oil.

Examples of colorants include carbon black, colcothar, and titanium oxide.

Examples of low-stress additives include silicone oil and silicone rubber.

Examples of metal hydroxides include hydroxides such as calcium hydroxide, aluminum hydroxide, and magnesium hydroxide.

In a case where the component (E), an inorganic filler, is comprised, a silane coupling agent may be compounded together.

The compounding ratio of such other component(s) is preferably in a range of 0.01 parts by mass or more and 10 parts by mass or less, more preferably in a range of 0.1 parts by mass or more and 7 parts by mass or less in terms of the compounding ratio of such other component(s) based on 100 parts by mass in total of the components (A), (B), and (C).

[Method of Producing Curable Resin Composition]

Next, the method of producing the curable resin composition of the present invention is described.

The curable resin composition of the present invention can be produced by kneading or mixing the components (A) to (D), and further, if desired, the components (E) to (F), other component(s) such as other additive(s), and a solvent, which are appropriately added.

The kneading or mixing method is not particularly limited, and the mixing can be made using, for example, a mixing apparatus or a kneading machine such as a planetary mixer, a twin-screw extruder, a heat roll or a kneader. For example, in the case where the components (A), (B), and (C) are highly viscous liquids or solids at room temperature or in the case where the component (E) is contained, if necessary, heating and kneading may be made or kneading may be made under a pressure or reduced pressure condition. The heating temperature is preferably 80 to 120° C.

The curable resin composition, which includes the component (E), is a solid at room temperature, and thus may be heated and kneaded, and thereafter cooled and pulverized to provide a powder, or the powder may be tabletted and thus formed into a pellet. The powder may also be granulated and thus formed into a granule.

In the case where the curable resin composition of the present invention, which does not contain any component (E), is used in an application of prepreg for FRP, the curable resin composition preferably has a viscosity of 10 to 3000 Pa·s at 50° C. The viscosity is more preferably 10 to 2500 Pa·s, still more preferably 100 to 2000 Pa·s. In the case where the curable resin composition of the present invention is used in a sealant or coating application, the viscosity is not particularly limited as long as working such as sealing or coating is not impaired.

[Cured Product]

The cured product of the curable resin composition of the present invention is characterized by being high in glass transition temperature, being excellent in heat resistance, and being excellent in mechanical strength. The reason why such an excellent cured product is formed by the curable resin composition of the present invention is considered as follows.

It is considered that a phenolic hydroxyl group is first produced by polymerization in homopolymerization of benzoxazine and the phenolic hydroxyl group undergoes a keto-enol tautomer at a high temperature, for example, 200° C. or more, thereby resulting in cleavage of a polymer chain, and thus causing lower heat resistance and also a lower glass transition temperature.

On the contrary, it is considered that the multifunctional epoxy compound having a norbornane structure and two or more epoxy groups, in the present invention, is hardly homopolymerized and reacts with the phenolic hydroxyl group derived from benzoxazine to thereby prevent the cleavage of a polymer chain. Thus, a cured product high in heat resistance is considered to be obtained.

In addition, using a biphenyl type epoxy compound in combination is considered to afford a cured product excellent in mechanical strength because the biphenyl structure has a marked effect in Imparting toughness.

(Characteristics of Cured Product)

The heat resistance of the cured product of the present invention can be evaluated by measuring the glass transition temperature. The glass transition temperature is, for example, 190° C. or more, preferably 200° C. or more, more preferably 210° C. or more. The glass transition temperature can be measured by differential scanning calorimetry (DSC). Such measurement can be simply performed by use of a commercially available differential scanning calorimeter (for example, manufactured by HITACHI HIGH-TECH SCIENCE CORPORATION).

The mechanical strength of the cured product of the present invention can be evaluated by measuring bending strength in a bending test. The bending strength in a bending test is, for example, 121 MPa or more, preferably 125 MPa or more, more preferably 130 MPa or more. The bending strength in a bending test can be measured in accordance with JIS K6911. Such measurement can be simply performed by use of a commercially available precision universal testing machine (for example, manufactured by SHIMADZU CORPORATION).

[Method of Producing Cured Product]

The cured product of the present invention can be produced by performing ring-opening polymerization for curing in the same curing conditions as in known benzoxazine compound and/or epoxy compound. Examples can include the following method.

The cured product can be obtained by first producing the curable resin composition of the present invention by the above method. Subsequently, heating the resulting curable resin composition can be heated at, for example, 150 to 300° C. for a curing time of, for example, 20 seconds to 5 hours, preferably 20 seconds to 1 hour, to obtain a cured product. While a treatment for a curing time of 1 to 3 minutes is sufficient for continuous production of the cured product, further heating for about 5 minutes to 5 hours in post-curing is preferable for achievement of higher strength.

The cured product can also be obtained by compounding a benzoxazine compound other than the component (A) and/or an epoxy compound other than the components (B) and (C), as long as the effects of the present invention are not impaired.

In the case where a film-shaped molded product is obtained as the cured product, a solvent can also be compounded to provide a composition which has a suitable viscosity for film formation. The solvent is not particularly limited as long as it can dissolve the components (A) to (D) and (F), and examples thereof include hydrocarbons, ethers, esters and halogen-containing solvents.

In the case of such a solution-type curable resin composition dissolved in the solvent, the cured product can be obtained by coating a substrate with the solution-type curable resin composition, thereafter volatilizing the solvent, and then performing thermal curing.

[Semiconductor Device]

The semiconductor device of the present invention is a semiconductor device where a semiconductor element is disposed in a cured product obtained by curing the curable resin composition of the present invention, the composition containing the components (A) to (D), and, if desired, the components (E), (F), and/or (an)other component(s). The semiconductor element is here usually supported and secured by a lead frame being a thin plate of a metallic material. The phrase "semiconductor element is disposed in a cured product" means that the semiconductor element is sealed by a cured product of the curable resin composition, and represents the state where the semiconductor element is covered with the cured product. In such a case, the entire semiconductor element may be covered, or the surface of the semiconductor element disposed on a base plate may be covered.

In the case where the semiconductor device is produced by sealing various electronic components such as a semiconductor element with the cured product of the present invention, the semiconductor device can be produced by performing a sealing step according to a conventional molding method such as transfer molding, compression molding, or injection molding.

EXAMPLES

Hereinafter, the present invention will be specifically described with reference to Examples and Comparative Examples, the present invention is not intended to be limited to such Examples.

<Component (A); Multifunctional Benzoxazine Compound>

The following (A1) to (A2) were used in the component (A).

(A1); Phenol-diaminodiphenylmethane (P-d)-type benzoxazine represented by the following formula (2-1) (manufactured by SHIKOKU CHEMICALS CORPORATION)

[Chem 19]

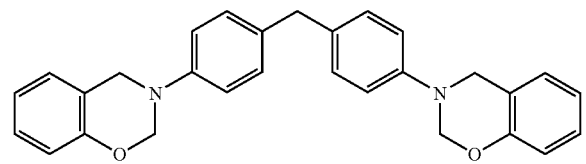

(2-1)

(A2); Bisphenol F-aniline (F-a)-type benzoxazine represented by the following formula (1-1) (manufactured by SHIKOKU CHEMICALS CORPORATION)

[Chem 23]

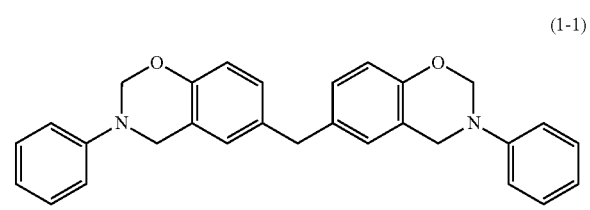

(1-1)

<Component (B); Alicyclic Epoxy Compound>

The following (B1) to (B3) were used in the component (B).

(B1) alicyclic epoxy compound 1; Compound of formula (5-1)

The compound (a) represented in formula (6) was synthesized according to a method described in "Shoichi Tsuchida et al., "Diels-Alder Reaction between Butadiene and Cyclopentadiene-Determination of Trimers-", Journal of the Japan Petroleum Institute, 1972, Vol. 15, Issue 3, pages 189 to 192".

Next, the reaction of formula (6) was performed as follows. A reaction vessel was charged with 23.5 kg of chloroform and 1.6 kg of the compound (a), and 4.5 kg of meta-chloroperbenzoic add was dropped thereto with stirring at 0° C. The temperature was raised to room temperature, and the reaction was performed for 12 hours.

Next, meta-chlorobenzoic acid as a by-product was removed by filtration, and thereafter the filtrate was washed with an aqueous 1 N sodium hydroxide solution three times and then washed with saturated saline. After the organic layer was dried over magnesium sulfate, the magnesium sulfate was removed by filtration and the filtrate was concentrated, thereby obtaining a crude product.

To the crude product was added 2 kg of toluene, and dissolved at room temperature. Thereto was dropped 6 kg of heptane for crystallization, and the resultant was aged at 5° C. for 1 hour. A crystallized product was collected by filtration and washed with hexane. The product was dried under reduced pressure at 35° C. for 24 hours, thereby obtaining 1.4 kg of a compound represented by the following formula (5-1), as a white solid.

[Chem 24]

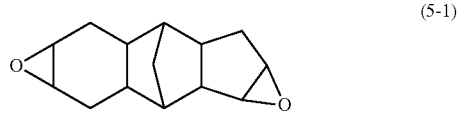

(5-1)

(B2) alicyclic epoxy compound 2; Compound (tricyclopentadiene diepoxide) of formula (5-2)

The compound (b) was synthesized as in the compound (a), according to the method described in the above Document.

Next, the reaction of formula (7) was performed as follows. A reaction vessel was charged with 59.2 kg of chloroform and 4.0 kg of the compound (b), and 10.6 kg of meta-chloroperbenzoic add was dropped thereto with stirring at −10° C. The temperature was raised to room temperature, and the reaction was performed for 12 hours.

Next, meta-chlorobenzoic acid as a by-product was removed by filtration, and thereafter the filtrate was washed with 42.0 kg of an aqueous 5% sodium sulfite solution. The organic layer was further washed with 41.6 kg of an aqueous 1 N sodium hydroxide solution four times, and thereafter washed with 48.0 kg of saturated saline. After the organic layer was dried over magnesium sulfate, the magnesium sulfate was removed by filtration and the filtrate was concentrated, thereby obtaining 5.1 kg of a crude product.

To the crude product was added 3.5 kg of toluene, and dissolved at room temperature. Thereto was dropped 13.7 kg of heptane for crystallization, and the resultant was aged at 5° C. for 1 hour. A crystallized product was collected by filtration and washed with heptane. The product was dried under reduced pressure at 35° C. for 12 hours, thereby obtaining 2.8 kg of a compound represented by the following formula (5-2), as a white solid.

[Chem 25]

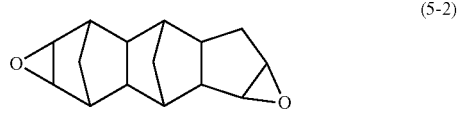

(5-2)

(B3) alicyclic epoxy compound 3; Compound (dicyclopentadiene diepoxide) of formula (5-4)

After a reaction vessel was charged with 10 kg of dicyclopentadiene, 68 kg of sodium bicarbonate, 100 L of acetone and 130 L of ion exchange water, and cooled to 10° C. or less, cooling was controlled so that the temperature of the reaction liquid was kept at 30° C. or less, and 84 kg of oxone was gradually added and the reaction was performed with stirring for 10 hours.

Next, the reaction product was extracted with 100 L of ethyl acetate twice, and the resulting organic layers were fractionated and combined. Subsequently, the organic layer combined was washed with 100 L of a mixed aqueous solution of saline and sodium thiosulfate (20% by weight of saline+20% by weight of sodium thiosulfate), and thereafter further washed with 100 L of ion exchange water twice.

After the organic layer washed was dried over magnesium sulfate, the magnesium sulfate was removed by filtration, and the organic solvent was distilled off from the filtrate, thereby obtaining 11 kg of a compound represented by the following formula (5-4), as a white solid.

[Chem 26]

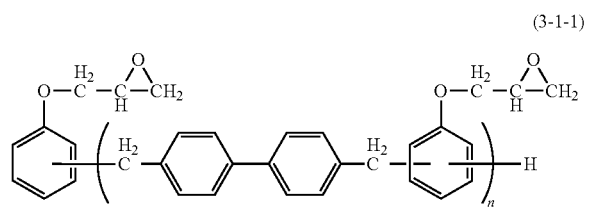

(5-4)

<Component (C); Biphenyl Type Epoxy Compound>

The following (C1) to (C2) were used in the component (C).

(C1); Biphenyl type epoxy compound (NC3000, having an epoxy equivalent (g/eq): 265 to 285, manufactured by NIPPON KAYAKU CO., LTD) represented by the following formula (3-1-1):

[Chem 27]

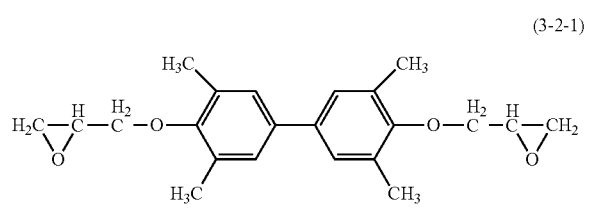

(3-1-1)

(wherein in the formula (3-1-1), n represents an average value and is 3.4).

(C2); Biphenyl type epoxy compound (YX4000H, having an epoxy equivalent (g/eq); 187 to 197, manufactured by MITSUBISHI CHEMICAL CORPORATION) represented by the following formula (3-2-1):

[Chem 28]

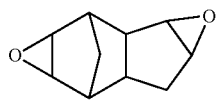

(3-2-1)

<Component (D); Curing Agent>

The following (D1) to (D4) were used in the component (D).

(D1); Bis(4-hydroxyphenyl)sulfide (TDP) represented by the following formula (9-1) (manufactured by TOKYO CHEMICAL INDUSTRY CO., LTD.)

[Chem 29]

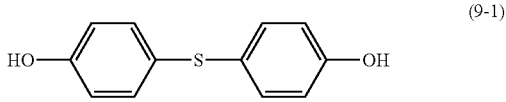

(9-1)

(D2); Bisohenol F represented by the following formula (9-2) (manufactured by HONSHU CHEMICAL INDUSTRY CO., LTD.)

[Chem 30]

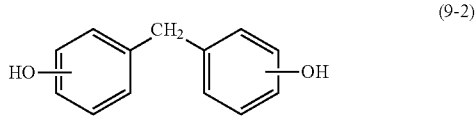

(9-2)

(D3); 2,7-dihydroxynaphthalene represented by the following formula (9-3) (manufactured by TOKYO CHEMICAL INDUSTRY CO., LTD.)

[Chem 31]

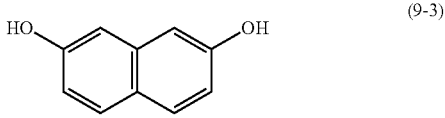

(9-3)

(D4); Pyrogallol represented by the following formula (9-4) (manufactured by TOKYO CHEMICAL INDUSTRY CO., LTD.)

[Chem 32]

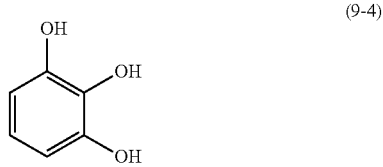

(9-4)

<Component (E); Inorganic Filler>

A molten spherical silica (FB 820, manufactured by DENKA COMPANY LIMITED) having an average particle size D50 of 22 μm was used in the component (E).

<Component (F); Curing Accelerator>

The following was used in the component (F).

(F); Triphenylphosphine (TPP) (manufactured by HOKKO CHEMICAL INDUSTRY CO., LTD.)

<Other Components>

Carnauba wax (manufactured by Clariant Japan K.K.) as a release agent and carbon black (MA600, manufactured by MITSUBISHI CHEMICAL CORPORATION) as a colorant were used.

Example 1

A curable resin composition (hereinafter, simply referred to as "composition") and a cured product were prepared as follows, and the glass transition temperature for heat resistance evaluation and the bending strength and bending modulus in a bending test for mechanical strength evaluation were measured.

After (A1), (B1), (C1), (D1), (E), (F), carnauba wax, and carbon black were kneaded at a compounding ratio shown in Table 1, by use of a heat roll kneader including respective two rods having surface temperatures of 90° C. and 100° C. (BR-150HCV, AIMEX CO., Ltd.), under atmospheric pressure for 10 minutes, the resultant was cooled to room temperature to obtain a mixture. The mixture was pulverized for powdering by Mini Speed Mill MS-09 (manufactured by LABONECT) so that packing into a mold was favorably performed, thereby obtaining a composition.

<Glass Transition Temperature; Tg>

A transfer molding machine was used to cure the composition prepared, in conditions of a mold temperature of 200° C., an injection pressure of 4 MPa and a curing time of 3 minutes, and the resultant was subjected to heating as a post-curing treatment in an oven at 240° C. for 4 hours, thereby producing a cured product of 3 mm length×3 mm width×15 mm height. The cured product was cut to provide a test piece having a size of 3 mm length×3 mm width×2 mm height, and the test piece was used to measure Tg by DSC in the following conditions. The results are shown in Table 1.

Apparatus: X-DSC-7000 (manufactured by HITACHI HIGH-TECH SCIENCE CORPORATION)

Measurement conditions: flow rate of $N_2$; 20 mL/min, rate of temperature rise; 20° C./min <Bending Strength and Bending Modulus>

A transfer molding machine was used to cure the composition prepared, in conditions of a mold temperature of 200° C., an injection pressure of 4 MPa and a curing time of 3 minutes, and the resultant was subjected to heating as a post-curing treatment in an oven at 240° C. for 4 hours, thereby producing a cured product of 10 mm width×80 mm length×3 mm thickness. The bending strength [MPa] and bending modulus [MPa] of the cured product were measured in accordance with ES K 6911 using a precision universal testing machine (AGS-1kNX, manufactured by SHIMADZU CORPORATION).

Examples 2 to 21

Each composition of the Examples was prepared in the same manner as in Example 1 except that the compounding ratio of each of the components was as shown in Table 1. Each composition was measured in the same manner as in Example 1 for heat resistance (glass transition temperature) and bending strength and bending modulus in a bending test. The results are shown in Table 1.

Comparative Examples 1 to 4

Each composition of Comparative Examples was prepared in the same manner as in Example 1 except that the compounding ratio of each of the components was as shown in Table 2. Each composition was measured in the same manner as in Example 1 for heat resistance (glass transition temperature) and bending strength and bending modulus in a bending test. The results are shown in Table 2.

TABLE 1

|  |  |  | Example 1 | Example 2 | Example 3 | Example 4 | Example 5 | Example 6 |
|---|---|---|---|---|---|---|---|---|
| Component (parts by mass) | Multifunctional Benzoxazine Compound 1 | (A1) | 6.4 | 6.0 | 5.6 | 5.8 | 5.4 | 6.9 |
|  | Multifunctional Benzoxazine Compound 2 | (A2) |  |  |  |  |  |  |
|  | Alicyclic Epoxy Compound 1 | (B1) | 5.0 | 4.4 | 3.8 |  |  |  |
|  | Alicyclic Epoxy Compound 2 | (B2) |  |  |  | 4.6 | 3.9 |  |
|  | Alicyclic Epoxy Compound 3 | (B3) |  |  |  |  |  | 3.7 |
|  | Biphenyl type Epoxy Compound 1 | (C1) | 0.6 | 1.5 | 2.5 | 1.5 | 2.6 | 1.2 |
|  | Biphenyl type Epoxy Compound 2 | (C2) |  |  |  |  |  |  |
|  | Curing Agent 1 | (D1) | 2.0 | 2.0 | 2.0 | 2.0 | 2.0 | 2.0 |
|  | Curing Agent 2 | (D2) |  |  |  |  |  |  |
|  | Curing Agent 3 | (D3) |  |  |  |  |  |  |
|  | Curing Agent 4 | (D4) |  |  |  |  |  |  |
|  | Inorganic Filler | (E) | 85.0 | 85.0 | 85.0 | 85.0 | 85.0 | 85.0 |
|  | Curing Accelerator | (F) | 0.5 | 0.5 | 0.5 | 0.5 | 0.5 | 0.5 |
|  | Carnauba wax |  | 0.3 | 0.3 | 0.3 | 0.3 | 0.3 | 0.3 |
|  | Carbon Black |  | 0.3 | 0.3 | 0.3 | 0.3 | 0.3 | 0.3 |
| Epoxy Equivalent Ratio |  |  | 1.0 | 1.0 | 1.0 | 1.0 | 1.0 | 1.0 |
| Performance Evaluation | Heat Resistance (Glass Transition Temperature) [° C.] |  | 250 | 243 | 222 | 241 | 220 | 208 |
|  | Bending Strength [MPa] |  | 134 | 147 | 156 | 145 | 155 | 138 |
|  | Bending Modulus [MP3] |  | 27000 | 27000 | 27000 | 27000 | 27000 | 27000 |

|  |  |  | Example 7 | Example 8 | Example 9 | Example 10 | Example 11 | Example 12 |
|---|---|---|---|---|---|---|---|---|
| Component (parts by mass) | Multifunctional Benzoxazine Compound 1 | (A1) | 6.4 | 6.2 | 5.9 | 5.9 | 7.6 | 5.8 |
|  | Multifunctional Benzoxazine Compound 2 | (A2) |  |  |  |  |  |  |

TABLE 1-continued

|  |  |  |  |  |  |  |  |
|---|---|---|---|---|---|---|---|
|  | Alicyclic Epoxy Compound 1 | (B1) |  | 4.3 | 3.6 | 3.6 | 3.8 | 5.5 |
|  | Alicyclic Epoxy Compound 2 | (B2) |  |  |  |  |  |  |
|  | Alicyclic Epoxy Compound 3 | (B3) | 3.3 |  |  |  |  |  |
|  | Biphenyl type Epoxy Compound 1 | (C1) | 2.2 |  |  | 1.2 | 0.4 | 0.6 |
|  | Biphenyl type Epoxy Compound 2 | (C2) |  | 1.4 | 2.4 | 1.2 |  |  |
|  | Curing Agent 1 | (D1) | 2.0 | 2.0 | 2.0 | 2.0 | 2.0 | 2.0 |
|  | Curing Agent 2 | (D2) |  |  |  |  |  |  |
|  | Curing Agent 3 | (D3) |  |  |  |  |  |  |
|  | Curing Agent 4 | (D4) |  |  |  |  |  |  |
|  | Inorganic Filler | (E) | 85.0 | 85.0 | 85.0 | 85.0 | 85.0 | 85.0 |
|  | Curing Accelerator | (F) | 0.5 | 0.5 | 0.5 | 0.5 | 0.5 | 0.5 |
|  | Carnauba wax |  | 0.3 | 0.3 | 0.3 | 0.3 | 0.3 | 0.3 |
|  | Carbon Black |  | 0.3 | 0.3 | 0.3 | 0.3 | 0.3 | 0.3 |
| Epoxy Equivalent Ratio |  |  | 1.0 | 1.0 | 1.0 | 1.0 | 0.7 | 1.2 |
| Performance | Heat Resistance (Glass Transition Temperature) [° C.] |  | 195 | 229 | 218 | 221 | 249 | 242 |
| Evaluation | Bending Strength [MPa] |  | 149 | 138 | 140 | 150 | 138 | 143 |
|  | Bending Modulus [MP3] |  | 27000 | 27000 | 27000 | 27000 | 27000 | 27000 |

|  |  |  | Example 13 | Example 14 | Example 15 | Example 16 | Example 17 |
|---|---|---|---|---|---|---|---|
| Component (parts by mass) | Multifunctional Benzoxazine Compound 1 | (A1) |  |  |  | 6.5 | 7.1 |
|  | Multifunctional Benzoxazine Compound 2 | (A2) | 6.4 | 6.0 | 5.6 |  |  |
|  | Alicyclic Epoxy Compound 1 | (B1) | 5.0 | 4.4 | 3.8 | 3.7 |  |
|  | Alicyclic Epoxy Compound 2 | (B2) |  |  |  |  |  |
|  | Alicyclic Epoxy Compound 3 | (B3) |  |  |  |  | 3.2 |
|  | Biphenyl type Epoxy Compound 1 | (C1) | 0.6 | 1.5 | 2.5 | 2.5 | 2.1 |
|  | Biphenyl type Epoxy Compound 2 | (C2) |  |  |  |  |  |
|  | Curing Agent 1 | (D1) | 2.0 | 2.0 | 2.0 |  |  |
|  | Curing Agent 2 | (D2) |  |  |  | 1.3 | 1.4 |
|  | Curing Agent 3 | (D3) |  |  |  |  |  |
|  | Curing Agent 4 | (D4) |  |  |  |  |  |
|  | Inorganic Filler | (E) | 85.0 | 85.0 | 85.0 | 85.0 | 85.0 |
|  | Curing Accelerator | (F) | 0.5 | 0.5 | 0.5 | 0.5 | 0.5 |
|  | Carnauba wax |  | 0.3 | 0.3 | 0.3 | 0.3 | 0.3 |
|  | Carbon Black |  | 0.3 | 0.3 | 0.3 | 0.3 | 0.3 |
| Epoxy Equivalent Ratio |  |  | 1.0 | 1.0 | 1.0 | 1.0 | 1.0 |
| Performance | Heat Resistance (Glass Transition Temperature) [° C.] |  | 210 | 202 | 193 | 225 | 200 |
| Evaluation | Bending Strength [MP3] |  | 132 | 141 | 151 | 153 | 151 |
|  | Bending Modulus [MP3] |  | 27000 | 27000 | 27000 | 27000 | 27000 |

|  |  |  |  | Example 18 | Example 19 | Example 20 | Example 21 |
|---|---|---|---|---|---|---|---|
| Component (parts by mass) | Multifunctional Benzoxazine Compound 1 | (A1) |  | 6.8 | 6.8 | 6.3 | 6.0 |
|  | Multifunctional Benzoxazine Compound 2 | (A2) |  |  |  |  |  |
|  | Alicyclic Epoxy Compound 1 | (B1) |  | 1.7 |  | 3.8 | 4.0 |
|  | Alicyclic Epoxy Compound 2 | (B2) |  |  | 1.7 |  |  |
|  | Alicyclic Epoxy Compound 3 | (B3) |  | 1.7 | 1.7 |  |  |
|  | Biphenyl type Epoxy Compound 1 | (C1) |  | 2.3 | 2.3 | 2.6 | 2.7 |
|  | Biphenyl type Epoxy Compound 2 | (C2) |  |  |  |  |  |
|  | Curing Agent 1 | (D1) |  |  |  |  |  |
|  | Curing Agent 2 | (D2) |  | 1.4 | 1.4 |  |  |
|  | Curing Agent 3 | (D3) |  |  |  | 1.3 |  |
|  | Curing Agent 4 | (D4) |  |  |  |  | 1.2 |

TABLE 1-continued

| | | | | | | |
|---|---|---|---|---|---|---|
| | Inorganic Filler | (E) | 85.0 | 85.0 | 85.0 | 85.0 |
| | Curing Accelerator | (F) | 0.5 | 0.5 | 0.5 | 0.5 |
| | Carnauba wax | | 0.3 | 0.3 | 0.3 | 0.3 |
| | Carbon Black | | 0.3 | 0.3 | 0.3 | 0.3 |
| Epoxy Equivalent Ratio | | | 1.0 | 1.0 | 1.0 | 1.0 |
| Performance | Heat Resistance (Glass Transition Temperature) [° C.] | | 219 | 221 | 215 | 221 |
| Evaluation | Bending Strength [MP3] | | 152 | 155 | 154 | 149 |
| | Bending Modulus [MP3] | | 27000 | 27000 | 27000 | 27000 |

TABLE 2

| | | | Comparative Example 1 | Comparative Example 2 | Comparative Example 3 | Comparative Example 4 |
|---|---|---|---|---|---|---|
| Component (parts by mass) | Multifunctional Benzoxazine Compound 1 | (A1) | 6.6 | 6.4 | 7.5 | |
| | Multifunctional Benzoxazine Compound 2 | (A2) | | | | 6.6 |
| | Alicyclic Epoxy Compound 1 | (B1) | 5.3 | | | 5.3 |
| | Alicyclic Epoxy Compound 2 | (B2) | | 5.5 | | |
| | Alicyclic Epoxy Compound 3 | (B3) | | | 4.4 | |
| | Biphenyl type Epoxy Compound 1 | (C1) | | | | |
| | Biphenyl type Epoxy Compound 2 | (C2) | | | | |
| | Curing Agent 1 | (D1) | 2.0 | 2.0 | 2.0 | 2.0 |
| | Inorganic Filler | (E) | 85.0 | 85.0 | 85.0 | 85.0 |
| | Curing Accelerator | (F) | 0.5 | 0.5 | 0.5 | 0.5 |
| | Carnauba wax | | 0.3 | 0.3 | 0.3 | 0.3 |
| | Carbon Black | | 0.3 | 0.3 | 0.3 | 0.3 |
| Epoxy Equivalent Ratio | | | 1.0 | 1.0 | 1.0 | 1.0 |
| Performance Evaluation | Heat Resistance (Glass Transition Temperature) [° C.] | | 257 | 248 | 223 | 217 |
| | Bending Strength [MPa] | | 120 | 119 | 110 | 113 |
| | Bending Modulus [MPa] | | 27000 | 27000 | 27000 | 27000 |

The cured product of the curable resin composition in each Example had a Tg of 190° C. or more, exhibiting high heat resistance, and had a bending strength of 121 MPa or more in a bending test, exhibiting excellent mechanical strength. In contrast, the cured product of the curable resin composition in each of Comparative Examples 1 to 4 had a low bending strength in a bending test, exhibiting low mechanical strength.

The above-mentioned results have revealed that a cured product of the curable resin composition according to an embodiment of the present invention has achieved high heat resistance and high mechanical strength.

The invention claimed is:

1. A curable resin composition containing:
   (A) a multifunctional benzoxazine compound having at least two benzoxazine rings, the compound being at least one multifunctional benzoxazine compound selected from a multifunctional benzoxazine compound having a structural unit of formula (1) and a multifunctional benzoxazine compound represented by a structure of formula (2),
   (B) an epoxy compound having at least one norbornane structure and at least two epoxy groups, wherein the epoxy compound (B) has at least one moiety selected from

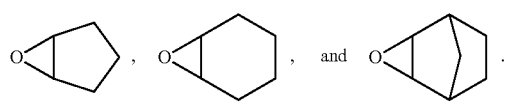

(C) a biphenyl epoxy compound, and
   (D) a curing agent;
   wherein formula (1) is

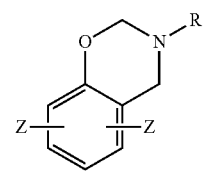

(1)

wherein in the formula (1), R represents a linear alkyl group having 1 to 12 carbon atoms, a cyclic alkyl group having 3 to 8 carbon atoms, or an aryl group having 6 to 14 carbon atoms, where the aryl group optionally has halogen or a linear alkyl group having 1 to 12 carbon atoms, as a substituent; and each Z represents hydrogen, a hydrocarbon group having 1 to 8 carbon atoms and/or a linking group and is optionally the same or different, at least one Z represents a linking group, and benzoxazine rings are linked by the linking group; and formula (2) is

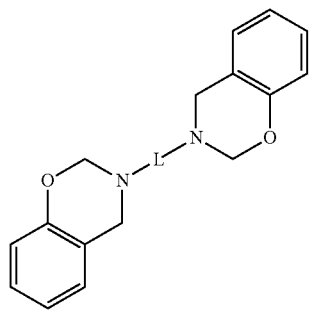

(2)

wherein in the formula (2), L represents a divalent organic group having 1 to 5 aromatic rings or an alkylene group having 2 to 10 carbon atoms, and the organic group and the alkylene group optionally comprise oxygen and/or sulfur.

2. The curable resin composition according to claim 1, wherein (C) the biphenyl epoxy compound is an epoxy compound represented by a structure of formula (3-1) or (3-2):

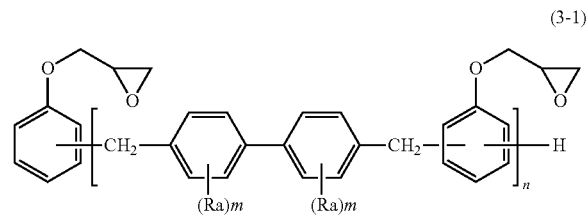

(3-1)

wherein in the formula (3-1), each substituent $R_a$ represents an alkyl group having 1 to 4 carbon atoms, optionally being the same or different; m represents the number of the substituent(s) $R_a$ and is an integer of 0 to 4; and n represents an average value and is 1 to 10;

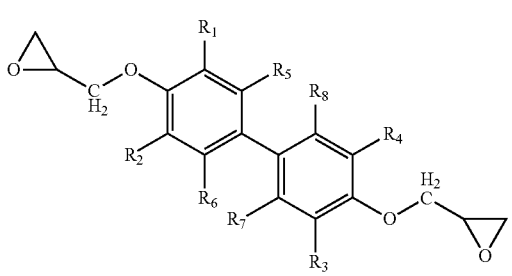

(3-2)

wherein in the formula (3-2), $R_1$ to $R_8$ represent a hydrogen atom, a halogen atom, or an alkyl group having 1 to 4 carbon atoms, and are each optionally the same or different.

3. The curable resin composition according to claim 2, further containing (E) an inorganic filler.

4. The curable resin composition according to claim 2, further containing (F) a curing accelerator.

5. A cured product obtained by curing the curable resin composition according to claim 2.

6. A semiconductor device, wherein a semiconductor element is disposed in a cured product obtained by curing the curable resin composition according to claim 2.

7. The curable resin composition according to claim 1, further containing (E) an inorganic filler.

8. The curable resin composition according to claim 7, further containing (F) a curing accelerator.

9. A cured product obtained by curing the curable resin composition according to claim 7.

10. A semiconductor device, wherein a semiconductor element is disposed in a cured product obtained by curing the curable resin composition according to claim 7.

11. The curable resin composition according to claim 1, further containing (F) a curing accelerator.

12. A cured product obtained by curing the curable resin composition according to claim 11.

13. A semiconductor device, wherein a semiconductor element is disposed in a cured product obtained by curing the curable resin composition according to claim 11.

14. A cured product obtained by curing the curable resin composition according to claim 1.

15. A semiconductor device, wherein a semiconductor element is disposed in a cured product obtained by curing the curable resin composition according to claim 1.

16. A method of producing a curable resin composition, the method comprising the steps of:
mixing
(A) a multifunctional benzoxazine compound having at least two benzoxazine rings, the compound being at least one multifunctional benzoxazine compound selected from a multifunctional benzoxazine compound having a structural unit of formula (1) and a multifunctional benzoxazine compound represented by a structure of formula (2),
(B) an epoxy compound having at least one norbornane structure and at least two epoxy groups, wherein the epoxy compound (B) has at least one moiety selected from

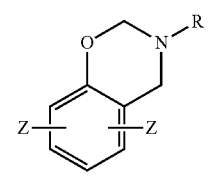

(1)

(C) a biphenyl epoxy compound, and
(D) a curing agent,
to obtain a mixture; and
processing the mixture into a powdery, pelletized, or granular curable resin composition;
wherein formula (1) is

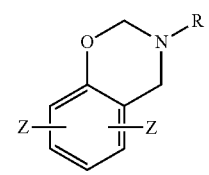

(1)

wherein in the formula (1), R represents a linear alkyl group having 1 to 12 carbon atoms, a cyclic alkyl group having 3 to 8 carbon atoms, or an aryl group having 6 to 14 carbon atoms, where the aryl group optionally has halogen or a linear alkyl group having 1 to 12 carbon atoms, as a substituent; and each Z represents hydrogen, a hydrocarbon group having 1 to 8 carbon atoms and/or a linking group and is optionally the same or different, at least one Z represents a linking group, and benzoxazine rings are linked by the linking group; and wherein formula (2) is

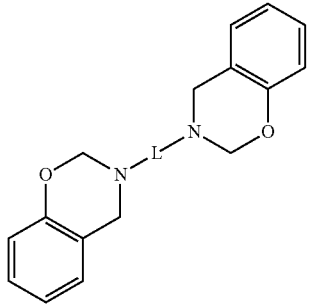

(2)

wherein in the formula (2), L represents a divalent organic group having 1 to 5 aromatic rings or an alkylene group having 2 to 10 carbon atoms, and the organic group and the alkylene group optionally comprise oxygen and/or sulfur.

17. The production method according to claim 16, wherein (C) the biphenyl epoxy compound is an epoxy compound represented by formula (3-1) or (3-2):

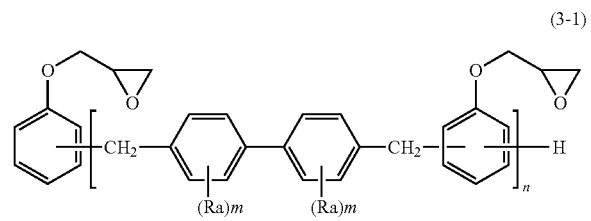

(3-1)

wherein in the formula (3-1), each substituent $R_a$ represents an alkyl group having 1 to 4 carbon atoms, optionally being the same or different; m represents the number of the substituent(s) $R_a$ and is an integer of 0 to 4; and n represents an average value and is 1 to 10;

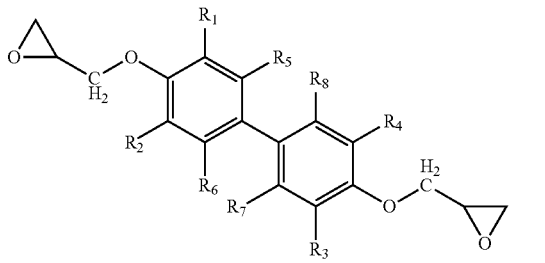

(3-2)

wherein in the formula (3-2), $R_1$ to $R_8$ represent a hydrogen atom, a halogen atom, or an alkyl group having 1 to 4 carbon atoms, and are each optionally the same or different.

18. The production method according to claim 17, wherein the step of obtaining a mixture comprises further mixing (E) an inorganic filler and/or (F) a curing accelerator to obtain a mixture.

19. The production method according to claim 16, wherein the step of obtaining a mixture comprises further mixing (E) an inorganic filler and/or (F) a curing accelerator to obtain a mixture.

20. A method of producing a cured product, the method comprising a step of heating the curable resin composition produced by the method according to claim 16, at 150 to 300° C. for 20 seconds to 1 hour for curing.

* * * * *